United States Patent
Kobayashi et al.

(10) Patent No.: US 10,738,004 B2
(45) Date of Patent: Aug. 11, 2020

(54) CYCLIC COMPOUND

(71) Applicant: Takeda Pharmaceutical Company Limited, Chuo-ku, Osaka-shi, Osaka (JP)

(72) Inventors: Toshitake Kobayashi, Kanagawa (JP); Morihisa Saitoh, Kanagawa (JP); Yasufumi Wada, Kanagawa (JP); Nobuyuki Negoro, Kanagawa (JP); Masashi Yamasaki, Kanagawa (JP); Takahiro Tanaka, Kanagawa (JP); Naomi Kitamoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 16/331,962

(22) PCT Filed: Sep. 7, 2017

(86) PCT No.: PCT/JP2017/032192
§ 371 (c)(1),
(2) Date: Mar. 8, 2019

(87) PCT Pub. No.: WO2018/047888
PCT Pub. Date: Mar. 15, 2018

(65) Prior Publication Data
US 2019/0233370 A1     Aug. 1, 2019

(30) Foreign Application Priority Data

Sep. 9, 2016 (JP) ................................ 2016-176545

(51) Int. Cl.
| | | |
|---|---|---|
| *C07C 317/46* | (2006.01) | |
| *A61K 31/235* | (2006.01) | |
| *A61P 1/16* | (2006.01) | |
| *A61P 9/10* | (2006.01) | |
| *A61P 37/02* | (2006.01) | |
| *A61P 29/00* | (2006.01) | |
| *A61P 25/02* | (2006.01) | |
| *A61P 43/00* | (2006.01) | |

(52) U.S. Cl.
CPC .......... *C07C 317/46* (2013.01); *A61K 31/235* (2013.01); *A61P 1/16* (2018.01); *A61P 9/10* (2018.01); *A61P 25/02* (2018.01); *A61P 29/00* (2018.01); *A61P 37/02* (2018.01); *A61P 43/00* (2018.01)

(58) Field of Classification Search
CPC ...... C07C 317/46; A61P 37/02; A61K 31/235
See application file for complete search history.

(56) References Cited

U.S. PATENT DOCUMENTS

| | | | |
|---|---|---|---|
| 6,495,604 B1 | 12/2002 | Ichimori et al. | |
| 7,078,540 B1 | 7/2006 | Tamura et al. | |
| 7,417,059 B2 | 8/2008 | Tamura et al. | |
| 7,935,835 B2 | 5/2011 | Kimura et al. | |
| RE43,858 E | 12/2012 | Kimura et al. | |
| 8,901,171 B2 | 12/2014 | Kitamoto | |
| 9,533,966 B2 | 1/2017 | Kobayashi et al. | |
| 9,611,244 B2 | 4/2017 | Kobayashi et al. | |
| 9,828,357 B2 | 11/2017 | Kobayashi et al. | |
| 9,869,533 B2 | 1/2018 | Vanarsdalen et al. | |
| 2005/0176783 A1 | 8/2005 | Tamura et al. | |
| 2006/0058288 A1 | 3/2006 | Ii et al. | |
| 2009/0062355 A1 | 3/2009 | Iizawa et al. | |
| 2009/0105314 A1 | 4/2009 | Ii et al. | |
| 2009/0233952 A1 | 9/2009 | Kimura et al. | |
| 2011/0184034 A1 | 7/2011 | Ii et al. | |
| 2012/0077856 A1 | 3/2012 | Iizawa et al. | |
| 2013/0046000 A1 | 2/2013 | Kitamoto | |
| 2013/0345304 A1 | 12/2013 | Kitamoto | |
| 2015/0051256 A1 | 2/2015 | Kitamoto | |
| 2015/0203464 A1 | 7/2015 | Kitamoto | |
| 2016/0076854 A1 | 3/2016 | Vanarsdalen et al. | |
| 2016/0166526 A1 | 6/2016 | Kitamoto | |
| 2016/0326102 A1 | 11/2016 | Kobayashi et al. | |
| 2016/0326133 A1 | 11/2016 | Kobayashi et al. | |
| 2017/0066737 A1 | 3/2017 | Kobayashi et al. | |
| 2018/0118708 A1 | 5/2018 | Kobayashi et al. | |

FOREIGN PATENT DOCUMENTS

| | | |
|---|---|---|
| JP | 2008-260760 A | 10/2008 |
| JP | 2013-518032 A | 5/2013 |
| WO | WO-99/46242 A1 | 9/1999 |
| WO | WO-01/10826 A1 | 2/2001 |

(Continued)

OTHER PUBLICATIONS

Dhillon, N. et al., "A single nucleotide polymorphism of Toll-like receptor 4 identifies the risk of developing graft failure after liver transplantation," Journal of Hepatology, Jul. 2010, vol. 53, No. 1, pp. 67-72.

Ilmakunnas, M. et al., "High Mobility Group Box 1 Protein as a Marker of Hepatocellular Injury in Human Liver Transplantation," Liver Transplantation, Oct. 2008, vol. 14, No. 10, pp. 1517-1525.

International Search Report for International Patent Application PCT/JP2017/032192 dated Nov. 28, 2017 (5 pages).

(Continued)

*Primary Examiner* — Rebecca L Anderson

(74) *Attorney, Agent, or Firm* — Foley & Lardner LLP

(57) ABSTRACT

Provided is a compound, such as ethyl 6-((2-chloro-4-fluorobenzyl)sulfonyl) -3-hydroxycyclohex-1-ene-1-carboxylate or an optical isomer thereof, having a superior Toll-like receptor 4 (TLR4) signaling inhibitory action, which may be useful as a prophylactic or therapeutic drug for diseases such as autoimmune diseases and/or inflammatory diseases, or chemotherapy-induced peripheral neuropathy (CIPN), chemotherapy-induced neuropathic pain (CINP), liver failure, and ischemia reperfusion injury (IRI).

20 Claims, No Drawings

(56) References Cited

FOREIGN PATENT DOCUMENTS

| WO | WO-03/084527 A1 | 10/2003 |
| WO | WO-2007/032362 A1 | 3/2007 |
| WO | WO-2007/123186 A1 | 11/2007 |
| WO | WO-2007/132825 A1 | 11/2007 |
| WO | WO-2016/181894 A1 | 11/2016 |
| WO | WO-2018/016657 A1 | 1/2018 |
| WO | WO-2018/047888 A1 | 3/2018 |

OTHER PUBLICATIONS

Yamada, M. et al., "Novel cyclohexene derivatives as anti-sepsis agents: Synthetic studies and inhibition of NO and cytokine production," Bioorganic & Medicinal Chemistry, 2008, vol. 16, No. 7, pp. 3941-3958.

Li et al., "Toll-Like Receptor 4 Signaling Contributes to Paclitaxel-Induced Peripheral Neuropathy," The Journal of Pain, Jul. 2014, 15(7):712-725.

CYCLIC COMPOUND

CROSS-REFERENCE TO RELATED APPLICATIONS

This application is a National Stage of application PCT/JP2017/032192, filed Sep. 7, 2017, which claims priority from Japanese application 2016-176545, filed Sep. 9, 2016.

TECHNICAL FIELD

The present invention relates to a novel cyclic compound having a Toll-like receptor 4 (TLR4) signaling inhibitory action, which may be useful as a prophylactic or therapeutic drug for diseases such as autoimmune diseases and/or inflammatory diseases, or chemotherapy-induced peripheral neuropathy (CIPN), chemotherapy-induced neuropathic pain (CINP), liver failure, and ischemia reperfusion injury (IRI), and use thereof.

BACKGROUND OF THE INVENTION

TLR4 was initially discovered as a receptor that recognizes lipopolysaccharide of gram negative bacteria and activates the innate immune system. However, in recent years, it has been clarified that it recognizes not only the innate immune response responsible for such infection defense but also various endogenous ligands produced in the aforementioned various diseases and activate various cells which play a central role in those diseases. In addition, it has been reported that expression of TLR4 is promoted in the lesions of various diseases, and development and progression of pathology in disease animal model such as TLR4 knockout mouse and mutant mouse are markedly suppressed. Therefore, TLR4 is suggested to play an important role in autoimmune disease and/or inflammatory diseases, or diseases such as cardiac diseases, renal diseases, hepatic diseases, central nervous system diseases, infectious diseases, malignant tumor, sepsis, and septic shock.

In addition to these diseases, the relationship with ischemia reperfusion injury (IRI) caused by resuming blood flow to an organ or tissue in an ischemic state, such as at the time of organ transplantation, has also been reported. High Mobility Group Box 1 (HMGB-1), which is one of the endogenous ligands of TLR4, increases in transplanted organs, and further, transplanted organs derived from donors having genetically hypofunctional TLR4 are resistant to dysfunction associated with IRI. Such known findings suggest that TLR4 signals caused by HMGB-1 play an important role in IRI (non-patent document 1, non-patent document 2).

From the above, a TLR4 signaling inhibitor (also referred to as "TLR4 inhibitor") is expected to be a prophylactic or therapeutic drug for diseases such as autoimmune diseases and/or inflammatory diseases, or cardiac diseases, renal diseases, hepatic diseases, central nervous system diseases, infectious diseases, malignant tumor, sepsis, and septic shock.

Patent document 1 reports the following compound:

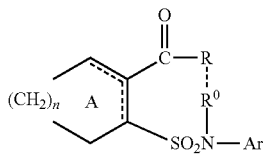

(Iaa)

[wherein each symbol is as described in the document] as a TLR4 signaling inhibitor.

Patent document 2 reports the following compound:

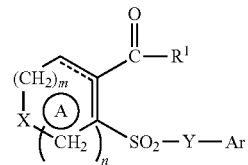

(I)

[wherein each symbol is as described in the document] as a TLR4 signaling inhibitor.

Patent documents 3 and 4 report the following compound:

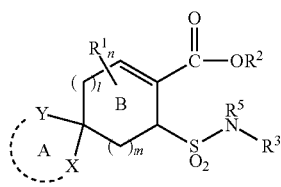

(I)

[wherein each symbol is as described in the documents] as a TLR4 signaling inhibitor.

In addition, the present Applicant reported as a TLR4 signaling inhibitor the following compound:

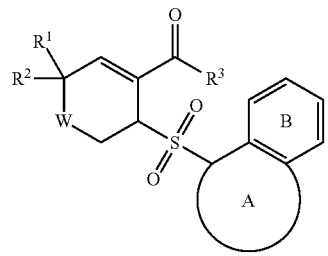

[wherein each symbol is as described in the document] in patent document 5, and the following compound:

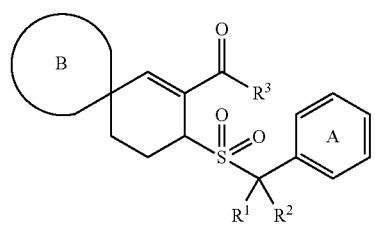

[wherein each symbol is as described in the document] in patent document 6.

DOCUMENT LIST

Non-Patent Documents

Non-patent document 1: Liver Transpl. 2008 October, 14(10), 1517-25 Non-patent document 2: J. Hepatol. 2010 July 53(1), 67-72

Patent Documents

Patent document 1: WO99/46242
Patent document 2: WO2001/010826
Patent document 3: WO2007/032362
Patent document 4: JP-A-2008-260760
Patent document 5: US-B-application Ser. No. 15/148,210
Patent document 6: International patent application No. PCT/JP2016/63628

SUMMARY OF THE INVENTION

Problems to be Solved by the Invention

The present invention aims to provide a compound having a superior TLR4 signaling inhibitory action, which may be useful as a prophylactic or therapeutic drug for diseases such as autoimmune diseases and/or inflammatory diseases, or chemotherapy-induced peripheral neuropathy (CIPN), chemotherapy-induced neuropathic pain (CINP), liver failure, and ischemia reperfusion injury (IRI).

Means of Solving the Problems

The present inventors have conducted intensive studies in an attempt to solve the above-mentioned problems and found that ethyl 6-((2-chloro-4-fluorobenzyl)sulfonyl)-3-hydroxycyclohex-1-en-1-carboxylate (hereinafter sometimes to be also abbreviated as "the compound of the present invention") or an optical isomer thereof has a superior TLR4 signaling inhibitory action, which resulted in the completion of the present invention.

Therefore, the present invention provides the following.

[1] Ethyl 6-((2-chloro-4-fluorobenzyl)sulfonyl)-3-hydroxycyclohex-1-en-1-carboxylate or an optical isomer thereof.
[2] cis-Ethyl 6-((2-chloro-4-fluorobenzyl)sulfonyl)-3-hydroxycyclohex-1-en-1-carboxylate or an optical isomer thereof.
[3] Ethyl (3S,6R)-6-((2-chloro-4-fluorobenzyl)sulfonyl)-3-hydroxycyclohex-1-en-1-carboxylate.
[4] A medicament comprising the compound of any of the above-mentioned [1] to [3].
[5] The medicament of the above-mentioned [4], which is a Toll-like receptor 4 inhibitor.
[6] The medicament of the above-mentioned [4], which is a prophylactic or therapeutic agent for an autoimmune disease and/or an inflammatory disease.
[7] The medicament of the above-mentioned [4], which is a prophylactic or therapeutic agent for chemotherapy-induced peripheral neuropathy (CIPN), chemotherapy-induced neuropathic pain (CINP), liver failure and/or ischemia reperfusion injury (IRI).
[8] The compound of any of the above-mentioned [1] to [3], which is used for preventing or treating an autoimmune disease and/or an inflammatory disease.
[9] The compound of any of the above-mentioned [1] to [3], which is used for preventing or treating chemotherapy-induced peripheral neuropathy (CIPN), chemotherapy-induced neuropathic pain (CINP), liver failure and/or ischemia reperfusion injury (IRI).
[10] A method for inhibiting a Toll-like receptor 4 in a mammal, comprising administering an effective amount of the compound of any of the above-mentioned [1] to [3] to the mammal.
[11] A method for preventing or treating an autoimmune disease and/or an inflammatory disease in a mammal, comprising administering an effective amount of the compound of any of the above-mentioned [1] to [3] to the mammal.
[12] A method for preventing or treating chemotherapy-induced peripheral neuropathy (CIPN), chemotherapy-induced neuropathic pain (CINP), liver failure and/or ischemia reperfusion injury (IRI) in a mammal, comprising administering an effective amount of the compound of any of the above-mentioned [1] to [3] to the mammal.
[13] Use of the compound of any of the above-mentioned [1] to [3] for the production of a prophylactic or therapeutic agent for an autoimmune disease and/or an inflammatory disease.
[14] Use of the compound of any of the above-mentioned [1] to [3] for the production of a prophylactic or therapeutic agent for chemotherapy-induced peripheral neuropathy (CIPN), chemotherapy-induced neuropathic pain (CINP), liver failure and/or ischemia reperfusion injury (IRI).

Effect of the Invention

The compound of the present invention has a Toll-like receptor 4 (TLR4) signaling inhibitory action, and may be useful as a prophylactic or therapeutic drug for diseases such as autoimmune diseases and/or inflammatory diseases, or chemotherapy-induced peripheral neuropathy (CIPN), chemotherapy-induced neuropathic pain (CINP), liver failure, and ischemia reperfusion injury (IRI).

DETAILED DESCRIPTION OF THE INVENTION

The present invention is explained in detail in the following.

The compound of the present invention is ethyl 6-((2-chloro-4-fluorobenzyl)sulfonyl)-3-hydroxycyclohex-1-en-1-carboxylate.

While the compound of the present invention may be a diastereomeric mixture, cis-ethyl 6-((2-chloro-4-fluorobenzyl)sulfonyl)-3-hydroxycyclohex-1-en-1-carboxylate is to preferable, and ethyl (3S,6R)-6-((2-chloro-4-fluorobenzyl)sulfonyl)-3-hydroxycyclohex-1-en-1-carboxylate is more preferable.

[Production Method]

The compound of the present invention can be produced by, for example, the method described in the Example.

When the compound of the present invention contains optical isomers, they are also included as the compound of the present invention, and each can be obtained as a single product by a synthetic method or a separation method (e.g., concentration, solvent extraction, column chromatography, recrystallization etc.) known per se. For example, a resolved optical isomer is also encompassed in the compound of the present invention.

The optical isomer can be produced by a method known per se. To be specific, an optical isomer is obtained by using an optically active synthetic intermediate, or by optical resolution of a racemate of the final product according to a conventional method.

As an optical resolution method, a method known per se, for example, fractional recrystallization, chiral column method and diastereomer method is used.

The compound of the present invention may be a crystal.

A crystal of the compound of the present invention can be produced by crystallizing the compound of the present invention by applying a crystallization method known per se.

Examples of the crystallization method include a method of crystallization from a solution, a method of crystallization from vapor, and a method of crystallization from a molten form.

A crystal of the compound of the present invention has high purity, high quality, and low hygroscopicity, is not denatured even after a long-term preservation under general conditions, and is extremely superior in the stability. In addition, it may be expected to be also superior in the biological properties (e.g., pharmacokinetics (absorption, distribution, metabolism, excretion), efficacy expression etc.) and may be useful as a medicament.

The prodrug of the compound of the present invention means a compound which is converted to the compound of the present invention by a reaction due to an enzyme, gastric acid and the like under the physiological condition in the living body, that is, a compound which is converted to the compound of the present invention by enzymatic oxidation, reduction, hydrolysis and the like; a compound which is converted to the compound of the present invention by hydrolysis and the like due to gastric acid, and the like. Examples of the prodrug for the compound of the present invention include a compound obtained by subjecting a hydroxy group in the compound of the present invention to acylation, alkylation, phosphorylation or boration (e.g., a compound obtained by subjecting a hydroxy group in the compound of the present invention to acetylation, palmitoylation, propanoylation, pivaloylation, succinylation, fumarylation, alanylation or dimethylaminomethylcarbonylation, and the like). These compounds can be produced from the compound of the present invention according to a method known per se.

The prodrug of the compound of the present invention may also be one which is converted to the compound of the present invention under physiological conditions as described in "IYAKUHIN no KAIHATSU (Development of Pharmaceuticals)", Vol. 7, Design of Molecules, p. 163-198, Published by HIROKAWA SHOTEN (1990).

The compound of the present invention may be a hydrate, a non-hydrate, a solvate or a non-solvate.

The compound of the present invention also encompasses a compound labeled with an isotope (e.g., $^3$H, $^{14}$C, $^{35}$S, $^{125}$I etc.) and the like.

Furthermore, the compound of the present invention also encompasses a deuterium conversion form wherein $^1$H is converted to $^2$H(D).

The compound of the present invention may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

The compound of the present invention may also be used as a PET tracer.

Since the compound of the present invention has a superior TLR4 signaling inhibitory action, it may also be useful as a safe medicament based on this action.

Therefore, the TLR4 signaling inhibitory substance in the present invention can be used for a mammal (e.g., mouse, rat, hamster, rabbit, cat, dog, bovine, sheep, monkey, human etc.) as a prophylactic or therapeutic agent for diseases such as autoimmune disease and/or inflammatory disease, or infectious disease, cardiac disease, central nervous system disease, immune hypofunction and the like, for example, sepsis including severe sepsis, septic shock, sepsis, endotoxic shock, exotoxin shock, systemic inflammatory response syndrome (SIRS), compensatory anti-inflammatory response syndrome (CARS), burn, trauma, post-surgical complications, cardiac failure, shock, hypotension, rheumatoid arthritis, osteoarthritis, gastritis, ulcerative colitis, peptic ulcer, stress-induced gastric ulcer, Crohn's disease, autoimmune disease, rejection after organ transplantation, ischemia reperfusion injury (IRI), liver failure (acute liver failure (ALI), ACLF), acute coronary microvascular embolism, shock vascular embolization (disseminated intravascular coagulation (DIC) and the like), ischemic cerebral disorder, arteriosclerosis, malignant anemia, Fanconi anemia, sickle cell anemia, pancreatitis, nephrotic syndrome, acute and chronic renopathy, nephritis, renal failure, insulin-dependent diabetes, non-insulin dependent diabetes, hepatic porphyria, alcoholism, Parkinson's disease, chronic leukemia, acute leukemia, tumor, myeloma, infant and adult respiratory distress syndrome, chronic obstructive pulmonary diseases, dementia, Alzheimer's disease, multiple sclerosis, neuromyelitis optica, vitamin E deficiency, aging, sunburn, muscular dystrophy, myocarditis, cardiomyopathy, myocardial infarction, myocardial infarction sequelae, osteoporosis, pneumonia, hepatitis, psoriasis, pain, cataract, influenza infections, malaria, human immunodeficiency virus (HIV) infections, radiation disorder, burn, hypercalcemia, ankylosing spondylitis, osteopenia, bone Paget's disease, osteomalacia, bone fracture, acute bacteria meningitis, *Helicobacter pylori* infectious disease, invasive staphylococcus infectious disease, tuberculosis, systemic fungal infectious diseases, herpes simplex virus infectious disease, varicella-zoster virus infectious disease, human papilloma virus infectious disease, acute viral encephalitis, encephalitis, meningitis, immune dysfunction associated with infections, bronchial asthma, atopic dermatitis, allergic rhinitis, reflux esophagitis, fever, hypercholesterolemia, hypertriglyceridemia, hyperlipidemia, diabetic complications, diabetic nephropathy, diabetic neuropathy, diabetic retinopathy, gout, gastric atony, hemorrhoids, systemic lupus erythematosus, spinal cord injury, insomnia, schizophrenia, epilepsy, cirrhosis of the liver, liver failure, unstable angina, heart valvular disease, thrombocytopenia or hypotension by dialysis, acute ischemic stroke, acute cerebral thrombosis, cancer metastasis, bladder cancer, breast cancer, cervical cancer, colorectal cancer, gastric cancer, ovarian cancer, prostate cancer, small cell lung cancer, non-small cell lung cancer, malignant melanoma, Hodgkin's disease, non-Hodgkin's lymphoma, side effects due to administration of anticancer drugs and immunosuppressants, chronic obstructive pulmonary diseases, cystic fibrosis, lung fibrosis, autoimmune hemolytic anemia, meningitis, inflammatory lung disease (e.g., silicosis, pulmonary sarcoidosis, pulmonary tuberculosis), endometriosis, cachexia (e.g., cachexia due to infection, cancer cachexia, cachexia induced by acquired immunodeficiency syndrome), cancer pain, Addison's disease, acute pain caused by inflammation, pain associated with chronic inflammation, postoperative pain (incision pain, deep pain, visceral pain, chronic pain after operation and the like), muscular pain (muscular pain associated with chronic pain disease, stiff shoulder and the like), arthralgia, toothache, temporomandibular joint pain, headache (migraine, catatonic headache, headache associated with fever, headache associated with hypertension), visceral pain (cardiac pain, angina pain, abdominal pain, renal pain, urinary tract pain, bladder pain), obstetric and gynecologic pain (mittelschmerz, dysmenorrhea, labor pain), neuropathic pain (hernia of intervertebral disk, nerve root pain, neuralgia after herpes zoster, trigeminal neuralgia, lumbago and the like), peripheral neuropathy (CIPN) derived from anticancer drugs (taxane anti-cancer agent (e.g., paclitaxel (taxol), docetaxel), *vinca* alkaloid anti-cancer agent (e.g., vincristine, vinblastine), platinum preparation (e.g., cisplatin, carboplatin, oxaliplatin), molecularly targeted drug (e.g., bortezomib) and the like) and neurological symptoms associated therewith (chemotherapy-induced neuropathic pain (CINP) (paresthesia such as numbness and/or pain (e.g., muscular pain, neuralgia))), reflex sympathetic atrophy, complex local pain syndrome, pituitary abscesses, thyroiditis, peritonitis, erythema nodosum), allergic conjunctivitis, pollinosis, metal allergy, otitis media exudative, Meniere's disease, contact dermatitis, anaphylaxis, urticaria, myasthenia gravis, Sjogren's syndrome, Basedow's disease, leukocyte abnormality, renal tubule stroma disorder (including fibrotic pathology), acute coronary artery syndrome, atherosclerotic aortic aneurysm, heart anaphylaxis, deep vein thrombosis, ocular disease (e.g., pterygium, spring catarrh, dry eye and the like), food allergy, NUD (Non Ulcer Dyspepsia), gastric MALT lymphoma, ulcer caused by non-steroidal anti-inflammatory agent, hyperacidity, hyperacidity and ulcer due to postoperative stress, obesity, edema, granulomatous, atopic myelitis, nerve fiber carcinoma, nasal mucosa hypersensitivity, osteoarthritis, scleroderma and the like. The TLR4 signaling inhibitory substance of the present invention may also be used for improving the efficiency of in vitro fertilization.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

A medicament containing the compound of the present invention can be used solely or by mixing with a pharmacologically acceptable carrier according to a method known per se (e.g., the method described in the Japanese Pharmacopoeia etc.) as the production method of a pharmaceutical preparation. The medicament containing the compound of the present invention may be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid (including organ preservation solution, perfusion fluid), emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, vicinity of tumor, lesion, and the like).

The content of the compound of the present invention in the medicament of the present invention is about 0.01 to 100% by weight of the whole medicament. While the dose varies depending on the subject of administration, administration route, disease and the like, for example, for an oral preparation to a patient (body weight about 60 kg) with chemotherapy-induced peripheral neuropathy (CIPN), chemotherapy-induced neuropathic pain (CINP), or liver failure and/or ischemia reperfusion injury (IRI), it is about 0.01 mg/kg body weight-about 500 mg/kg body weight, preferably about 0.1 mg/kg body weight-about 50 mg/kg body weight, further preferably about 1 mg/kg body weight-about 30 mg/kg body weight, as an active ingredient (the compound of the present invention) per one day, which is administered in one to several portions per day.

The pharmacologically acceptable carrier, which may be used for the production of the medicament of the present invention, may be exemplified by various organic or inorganic carrier substances that are conventionally used as pharmaceutical materials, for example, excipient, lubricant, binding agent and disintegrant for solid preparations; or solvent, solubilizing agent, suspending agent, isotonic agent, buffering agent, and soothing agent for liquid preparations. Furthermore, when necessary, ordinary additives such as preservative, antioxidant, colorant, sweetening agent, adsorbing agent, and wetting agent may also be used as appropriate in an appropriate amount.

The dose of the medicament of the present invention as a sustained-release preparation varies depending on the kind and content of the compound of the present invention, dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of the compound of the present invention needs to be released from the administered preparation per 1 week.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride and glycerin monostearate; hydrophilic polymers such as poly(vinyl alcohol), polyvinylpyrrolidone, carboxymethylcellulose sodium, methylcellulose, hydroxymethylcellulose, hydroxyethylcellulose and hydroxypropylcellulose; and the like.

Examples of the isotonic agent include glucose, D-sorbitol, sodium chloride, glycerin, D-mannitol and the like.

Examples of the buffering agent include buffer solutions such as phosphates, acetates, carbonates and citrates, and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention may also be used together with other medicaments. In the following, a medicament to be used when the compound of the present invention is used together with other drug is referred to as "the combination agent of the present invention".

The compound of the present invention may be used in combination with other drugs. Examples of such concomitant drug include antimicrobial drugs, antifungal drugs, non-steroidal antiinflammatory drugs, steroid drugs, anticoagulants, anti-platelet drugs, thrombolytic drugs, immunomodulators, antiprotozoal drugs, antitussives and expectorant drugs, sedatives, anesthetics, antinarcotics, antiulcer drugs, therapeutic drugs for hyperlipidemia, therapeutic drugs for arteriosclerosis, HDL-raising drugs, unstable plaque stabilizing drugs, myocardial protective drugs, therapeutic drugs for hypothyroidism, therapeutic drugs for nephrotic syndrome, therapeutic drugs for chronic renal failure, diuretics, antihypertensives, therapeutic drugs for cardiac failure, muscle relaxants, antiepileptic drugs, cardiotonic drugs, vasodilators, vasoconstrictors, therapeutic drugs for arrhythmia, therapeutic drugs for diabetes, vasopressors, tranquilizers, antipsychotic drugs, therapeutic drugs for Alzheimer's disease, anti-parkinsonian drugs, therapeutic drugs for amyotrophic lateral sclerosis, neurotrophic factors, antidepressants, therapeutic drugs for schizophrenia, anticancer agents, vitamins, vitamin derivatives, therapeutic drugs for arthritis, anti-rheumatic drugs, antiallergic drugs, antiasthmatic drugs, therapeutic drugs for atopic dermatitis, therapeutic drugs for allergic rhinitis, therapeutic drugs for pollakisuria or anischuria, proteolytic drugs, protease inhibitors, anti-SIDS drugs, anti sepsis drugs, anti septic shock drugs, endotoxin antagonists or antibodies, signal transduction inhibitors, inflammatory mediator action suppressors, antibodies to suppress inflammatory mediator action, inflammatory mediator production suppressors, anti-inflammatory mediator action suppressors, anti-antibodies to suppress anti-inflammatory mediator action, anti-inflammatory mediator production suppressors, al adrenergic agonists, anti-emetics, methemoglobin increase inhibitors and the like. Among these, anticancer agents, antibiotics, antifungal drugs, non-steroidal antiinflammatory drugs, steroid drugs, anticoagulants, anti-emetics, methemoglobin increase inhibitors and the like are preferable. Specifically, the following can be mentioned.

(1) Antimicrobial Drugs
(i) Sulfa drugs

Sulfamethizole, sulfisoxazole, sulfamonomethoxine, sufamethizole, salazosulfapyridine, silver sulfadiazine and the like.

(ii) Quinoline antimicrobial drugs

Nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.

(iii) Antitubercular drugs

Isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.

(iv) Therapeutic drugs for anti-fast bacterium disease

Diaminodiphenyl sulfone, rifampicin and the like.

(v) Antiviral drugs

Idoxuridine, acyclovir, vidarabine, gancyclovir and the like.

(vi) Anti-HIV drugs

Zidovudine, didanosine, zalcitabine, indinavir sulfate ethanolate, ritonavir and the like.

(vii) Antispirochetele (viii) Antibiotics

Tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidins [Journal of Antibiotics (J. Antibiotics), 38, 877-885 (1985)] and the like.

(2) Antifungal Drugs
(i) Polyene antibiotics (e.g., amphotericin B, nystatin, trichomycin).
(ii) Griseofulvin, pyrrolnitrin and the like.
(iii) Cytosine antimetabolites (e.g., flucytosine).
(iv) Imidazole derivatives (e.g., econazole, clotrimazole, miconazole nitrate, bifonazole, croconazole).
(v) Triazole derivatives (e.g., fluconazole, itraconazole, azole compound[2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone]).
(vi) Thiocarbamate derivatives (e.g., tolnaftate).
(vii) Echinocandin derivatives (e.g., caspofungin, micafungin, anidulafungin) and the like.

(3) Non-Steroidal Antiinflammatory Drugs

Acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone, meloxicam, celecoxib, rofecoxib or a salt thereof and the like.

(4) Steroid Drugs

Dexamethasone, hexestrol, methimazole, betamethasone, triamcinolone, triamcinolone acetonide, fluocinonide, fluocinolone acetonide, predonisolone, methylprednisolone, cortisone acetate, hydrocortisone, fluorometholone, beclomethasone dipropionate, estriol and the like.

(5) Anticoagulants

Heparin sodium, sodium citrate, activated protein C, tissue factor pathway inhibitor, antithrombin III, dalteparin sodium, warfarin potassium, argatroban, gabexate, sodium citrate and the like.

(6) Anti-Platelet Drugs

Sodium ozagrel, ethyl icosapentate, beraprost sodium, alprostadil, ticlopidine hydrochloride, pentoxifylline, dipyridamole and the like.

(7) Thrombolytic Drugs

Tisokinase, urokinase, streptokinase and the like.

(8) Immunomodulators

Cyclosporine, tacrolimus, gusperimus, azathioprine, anti-lymphocyte serum, dried sulfonated immunoglobulin, erythropoietin, colony stimulating factor, interleukin, interferon and the like.

(9) Antiprotozoal Drugs

Metronidazole, tinidazole, diethylcarbamazine citrate, quinine hydrochloride, quinine sulfate and the like.

(10) Antitussives and Expectorant Drugs

Ephedrine hydrochloride, noscapine hydrochloride, codeine phosphate, dihydrocodeine phosphate, isoproterenol hydrochloride, methylephedrine hydrochloride, alloclamide, chlophedianol, picoperidamine, cloperastine, protokylol, isoproterenol, salbutamol, terbutaline, oxypetebanol, morphine hydrochloride, dextropethorfan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(11) Sedatives

Chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(12) Anesthetics (12-1) Local Anesthetics

Cocaine hydrochloride, procaine hydrochloride, lidocain, dibucaine hydrochloride, tetracaine hydrochloride, mepivacaine hydrochloride, bupivacaine hydrochloride, oxybupro-caine hydrochloride, ethyl aminobenzoate, oxethazaine and the like.

(12-2) General anesthetics (i) Inhalation anesthetics (e.g., ether, halothane, nitrous oxide, isoflurane, enflurane), (ii) Intravenous anesthetics (e.g., ketamine hydrochloride, droperidol, thiopental sodium, thiamylal sodium, pentobarbital) and the like.

(13) Antinarcotics

Levallorphan, nalorphine, naloxone or a salt thereof and the like.

(14) Antiulcer Drugs

Metoclopramide, histidine hydrochloride, lansoprazole, metoclopramide, pirenzepine, cimetidine, ranitidine, famotidine, urogastrine, oxethazaine, proglumide, omeprazole, sucralfate, sulpiride, cetraxate, gefarnate, aldioxa, teprenone, prostaglandin and the like.

(15) Therapeutic Drugs for Hyperlipidemia

HMG-CoA reductase inhibitors (e.g., fluvastatin, cerivastatin, atorvastatin and the like), fibrates drugs (e.g., simfibrate, clofibrate aluminum, clinofibrate, fenofibrate and the like), bile acid adsorption drugs (e.g., colestyramine and the like), nicotinic acid preparations (e.g., nicomol, niceritrol, tocopherol nicotinate and the like), probucol and a derivative thereof, polyunsaturated fatty acid derivatives (e.g., ethyl icosapentate, polyene phosphatidyl choline, melinamide and the like), phytosterols (e.g., gamma-oryzanol, soysterol and the like), elastase, sodium dextran sulfate, squalene synthase inhibitor, squalene epoxydase inhibitor, CETP inhibitor, ethyl 2-chloro-3-[4-(2-methyl-2-phenyl-propoxy)phenyl]propionate [Chemical and Pharmaceutical Bulletin (Chem. Pharm. Bull), 38, 2792-2796 (1990)], LDL receptor increasing drug, cholesterol absorption inhibitors (Ezetimibe and the like), MTP inhibitor, intestinal bile acid transporter inhibitor, SCAP ligands, FXR ligands and the like.

(16) Therapeutic Drugs for Arteriosclerosis

MMP inhibitor, chymase inhibitor, ACAT inhibitor (Avasimibe, Eflucimibe and the like), apoAI Milano and analogs thereof, scavenger receptor inhibitor, 15-lipoxygenase inhibitor, phospholipase A2 inhibitor, ABCA1 activator, LXR ligand, sphingomyelinase inhibitor, paraoxonase activator, estrogen receptor agonist and the like.

(17) HDL-Raising Drugs

Squalene synthase inhibitor, CETP inhibitor, LPL activator and the like.

(18) Unstable Plaque Stabilizing Drugs

MMP inhibitor, chymase inhibitor, ACAT inhibitor, lipid-rich plaque regressing agent and the like.

(19) Myocardial Protective Drugs

Oral drug for Heart ATP-K, endothelin antagonist, urotensin antagonist and the like.

(20) Therapeutic Drugs for Hypothyroidism

Dried thyroid (thyreoid), levothyroxine sodium (thyrodin S), liothyronine sodium (thyronine, thyromine) and the like.

(21) Therapeutic Drugs for Nephrotic Syndrome

Predonisolone (predonine), predonisolone sodium succinate (water-soluble predonine), methylprednisolone sodium succinate (solu-medrol), betamethasone (rinderon) and the like.

(22) Therapeutic Drugs for Chronic Renal Failure

Diuretics [e.g., furosemide (lasix), bumetanide (lunetoron), azosemide (diart)], depressors [e.g., ACE inhibitor, enalapril maleate (renivace), calcium channel antagonist (manidipine), a receptor blockers, AII antagonist (candesartan)] and the like.

(23) Diuretics

Thiazide diuretics (benzylhydrochlorothiazide, cyclopenthiazide, ethiazide, hydrochlorothiazide, hydroflumethiazide, methyclothiazide, penfluthiazide, polythiazide, trichlormethiazide and the like), loop diuretics (chlortalidone, clofenamide, indapamide, mefruside, meticrane, sotolazone, tribamide, quinetazone, metolazone, furosemide and the like), potassium-sparing diuretics (spironolactone, triamterene and the like).

(24) Therapeutic Drugs for Hypertension (i) Sympathetic nerve inhibitors $\alpha_2$ Stimulants (e.g., clonidine, guanabenz, guanfacine, methyldopa and the like), ganglionic blockers (e.g., hexamethonium, trimethaphan and the like), presynaptic blockers (e.g., alseroxylon, dimethylaminoreserpinate, rescinnamine, reserpine, syrosingopine and the like), neuron blockers (e.g., betanidine, guanethidine and the like), $\alpha_1$ blockers (e.g., bunazosin, doxazosin, prazosin, terazosin, urapidil and the like), β blockers (e.g., propranolol, nadolol, timolol, nipradilol, bunitrolol, indenolol, penbutolol, carteolol, carvedilol, pindolol, acebutolol, atenolol, bisoprolol, metoprolol, labetalol, amosulalol, arotinolol and the like) and the like.

(ii) Vasodilators

Calcium channel antagonists (e.g., manidipine, nicardipine, nilvadipine, nisoldipine, nitrendipine, benidipine, amlodipine, aranidipine and the like), phthalazine derivatives (e.g., budralazine, cadralazine, ecarazine, hydralazine, todralazine and the like) and the like.

(iii) ACE inhibitors

Alacepril, captopril, cilazapril, delapril, enalapril, lisinopril, temocapril, trandolapril, quinapril, imidapril, benazepril, perendopril and the like.

(iv) AII antagonists

Losartan, candesartan, valsartan, telmisartan, irbesartan, forasartan and the like.

(v) Diuretics (e.g., the aforementioned diuretics and the like)

(25) Therapeutic Drugs for Cardiac Failure

Cardiotonic drugs (e.g., digitoxin, digoxin, methyldigoxin, lanatoside C, proscillaridin and the like), α, β stimulants (e.g., epinephrine, norepinephrine, isoproterenol, dopamine, docarpamine, dobutamine, denopamine and the like), phosphodiesterase inhibitors (e.g., amrinone, milrinone, olprinone hydrochloride and the like), calcium channel sensitizers (e.g., pimobendan and the like), nitrate drugs (e.g., nitroglycerin, isosorbide dinitrate and the like), ACE inhibitors (e.g., the aforementioned ACE inhibitors and the like), diuretics (e.g., the aforementioned diuretics and the like), carperitide, ubidecarenone, vesnarinone, aminophylline and the like.

(26) Muscle Relaxants

Pridinol, tubocurarine, pancuronium, tolperisone hydrochloride, chlorphenesin carbamate, baclofen, chlormezanone, mephenesin, chlorzoxazone, eperisone, tizanidine and the like.

(27) Antiepileptics

Phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(28) Cardiotonic Drugs

Aminophylline, etilefrine, dopamine, dobutamine, denopamine, aminophylline, amrinone, pimobendan, ubidecarenone, digitoxin, digoxin, methyldigoxin, lanatoside C, G-strophanthin and the like.

(29) Vasodilators

Oxyfedrine, diltiazem, tolazoline, hexobendine, bamethan, clonidine, methyldopa, guanabenz and the like.

(30) Vasoconstrictors

Dopamine, dobutamine, denopamine and the like.

(31) Therapeutic Drugs for Arrhythmia (i) Sodium channel blockers (e.g., quinidine, procainamide, disopyramide, ajmaline, cibenzoline, lidocaine, diphenylhydantoin, mexiletine, propafenone, flecainide, pilsicainide, phenytoin and the like), (ii) β Blockers (e.g., propranolol, alprenolol, bufetolol, oxprenolol, atenolol, acebutolol, metoprolol, bisoprolol, pindolol, carteolol, arotinolol and the like), (iii) Potassium channel blockers (e.g., amiodarone and the like), (iv) Calcium channel blockers (e.g., verapamil, diltiazem and the like) and the like.

(32) Vasopressors

Dopamine, dobutamine, denopamine, digitoxin, digoxin, methyldigoxin, lanatoside C, G-strophanthin and the like.

(33) Therapeutic Drugs for Diabetes

Sulfonylureas (e.g., tolbutamide, chlorpropamide, glyclopyramide, acetohexamide, tolazamide, glibenclamide, glybuzole and the like), biguanides (e.g., metformin hydrochloride, buformin hydrochloride and the like), α-glucosidase inhibitors (e.g., voglibose, acarbose and the like), insulin sensitizers (e.g., pioglitazone, rosiglitazone, troglitazone and the like), insulin, glucagon, therapeutic drug for diabetic complications (e.g., epalrestat and the like), DPP4 inhibitors (e.g., sitagliptin, vildagliptin, alogliptin, linagliptin and the like) and the like.

(34) Tranquilizers

Diazepam, lorazepam, oxazepam, chlordiazepoxide, medazepam, oxazolam, cloxazolam, clotiazepam, bromazepam, etizolam, fludiazepam, hydroxyzine and the like.

(35) Antipsychotic Drugs

Chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(36) Therapeutic Drugs for Alzheimer's Disease (i) Cholinesterase inhibitors such as donepezil, rivastigmine and galanthamine, (ii) cerebral function enhancers such as idebenone, memantine and vinpocetine.

(37) Anti-Parkinsonian Drugs

L-Dopa, deprenyl, carbidopa+levodopa, pergolide, ropinirole, cabergoline, pramipexole, entacapone, lazabemide and the like.

(38) Therapeutic Drugs for Amyotrophic Lateral Sclerosis

Riluzole, mecasermin, gabapentin and the like.

(39) Antidepressants

Imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(40) Therapeutic Drugs for Schizophrenia

Olanzapine, risperidone, quetiapine, iloperidone and the like.

(41) Anticancer Agents

6-O—(N-Chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate, paclitaxel, docetaxel, oxaliplatin, vincristine, vinblastine, carboplatin, bortezomib and the like.

(42) Vitamins (i) Vitamin A: vitamin $A_1$, vitamin $A_2$ and retinol palmitate.

(ii) Vitamin D: vitamin $D_1$, $D_2$, $D_3$, $D_4$ and $D_5$.

(iii) Vitamin E: α-tocopherol, β-tocopherol, γ-tocopherol, δ-tocopherol, dl-α-tocopherol nicotinate.

(iv) Vitamin K: vitamin $K_1$, $K_2$, $K_3$ and $K_4$.

(v) Folic acid (vitamin M).

(vi) Vitamin B: vitamin $B_1$, vitamin $B_2$, vitamin $B_3$, vitamin $B_5$, vitamin $B_6$ and vitamin $B_{12}$.

(vii) Biotin (vitamin H) and the like.

(43) Vitamin Derivatives

Various derivatives of vitamins, for example, ascorbic acid, 5,6-trans-cholecalciferol, 2,5-hydroxycholecalciferol, vitamin $D_3$ derivatives such as 1-a-hydroxycholecalciferol, vitamin $D_2$ derivatives such as 5,6-trans-ergocalciferol, and the like.

(44) Antiallergic Drugs

Diphenhydramine, chlorpheniramine, tripelennamine, clemizole, diphenylpyraline, methoxyphenamine, sodium cromoglicate, tranilast, repirinast, amlexanox, ibudilast, ketotifen, terfenadine, mequitazine, azelastine, epinastine, ozagrel hydrochloride, pranlukast hydrate, seratrodast and the like.

(45) Antiasthmatic Drugs

Isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, ibudilast, ketotifen, terfenadine, mequitazine, azelastine, epinastine, ozagrel hydrochloride, pranlukast hydrate, seratrodast, dexamethasone, predonisolone, hydrocortisone, beclomethasone dipropionate and the like.

(46) Therapeutic Drugs for Atopic Dermatitis

Sodium cromoglicate and the like.

(47) Therapeutic Drugs for Allergic Rhinitis

Sodium cromoglicate, chlorpheniramine maleate, alimemazine tartrate, clemastine fumarate, homochlorcyclizine hydrochloride, terfenadine, mequitazine and the like.

(48) Therapeutic Drugs for Pollakisuria or Anischuria

Flavoxate hydrochloride and the like.

(49) Anti-Sepsis Drugs

Peptidic compounds such as rBPI-21 (bactericidal permeability-increasing protein), BI-51017 (antithrombin III), SC-59735 (rTFPI), r-PAF acetylhydrolase, LY-203638 (r-activated protein C), anti-TNF-α antibody, anti-CD14 antibody, CytoFab and alkaline phosphatase (LPS inactivator), nonpeptidic compounds such as JTE-607, eritoran, S-5920, FR-167653, ONO-1714, ONO-5046 (sivelestat), GW-273629, RWJ-67657, GR-270773, NOX-100, GR-270773, NOX-100 and INO-1001, and the like.

(50) Prognosis Improving Agents after Coronary Bypass Surgery

Eritoran and the like.

(51) Antiemetics

Phenothiazine derivative, 5-HT3 receptor antagonist and the like.

(52) Methemoglobin Formation Inhibitors

Methylene blue, ascorbic acid and the like.

(53) Anti-Cytokine Drugs (I) Protein preparations (i) TNF inhibitors

Etanercept, infliximab, adalimumab, certolizumab pegol, golimumab, PASSTNF-α, soluble TNF-α receptor, TNF-α binding protein, anti-TNF-α antibody and the like.

(ii) Interleukin-1 inhibitors

Anakinra (interleukin-1 receptor antagonists), soluble interleukin-1 receptor and the like.

(iii) Interleukin-6 inhibitors

Tocilizumab (anti-interleukin-6 receptor antibody), anti-interleukin-6 antibody and the like.

(iv) Interleukin-10 drugs

Interleukin-10 and the like.

(v) Interleukin-12/23 inhibitors

Ustekinumab, briakinumab (anti-interleukin-12/23 antibody) and the like.

(vi) Interleukin-17 inhibitors

Secukinumab, ixekizumab, brodalumab and the like.

(II) Non-protein preparations (i) MAPK inhibitors

BMS-582949 and the like.

(ii) Gene modulators

Inhibitors of molecules involved in signal transduction such as NF-κ, NF-κB, IKK-1, IKK-2 and AP-1.

(iii) Cytokine production inhibitors

Iguratimod, tetomilast and the like.

(iv) TNF-α converting enzyme inhibitors (v) Interleukin-1β converting enzyme inhibitors VX-765 and the like.

(vi) Interleukin-6 antagonists

HMPL-004 and the like.

(vii) Interleukin-8 inhibitors

IL-8 antagonist, CXCR1 & CXCR2 antagonist, cephalexin and the like.

(viii) Chemokine antagonists

CCR9 antagonists (CCX-282, CCX-025), MCP-1 antagonist and the like.

(ix) Interleukin-2 receptor antagonists

Denileukin, diftitox and the like.

(x) Therapeutic vaccines

TNF-α vaccine and the like.

(xi) Gene therapy drugs

Gene therapy drugs aiming at enhancing the expression of genes having anti-inflammatory action such as interleukin-4, interleukin-10, soluble interleukin-1 receptor and soluble TNF-α receptor.

(xii) Antisense compounds

ISIS-104838 and the like.

(54) Integrin Inhibitors

Natalizumab, vedolizumab, AJM300, TRK-170, E-6007 and the like.

Antidepressants (e.g., amitriptyline, imipramine, clomipramine, desipramine, doxepin, nortriptyline, duloxetine, milnacipran, fluoxetine, paroxetine, sertraline, citalopram and the like).

Anticonvulsants (e.g., carbamazepine, pregabalin, gabapentin, lamotrigine, phenytoin, valproic acid and the like) Narcotics (e.g., morphine, oxycodone, fentanyl, methadone, codeine, tramadol and the like).

(55) Others

Hydroxicam, diacerein, megestrol acetate, nicergoline, prostaglandins and the like.

For combined use, the administration time of the compound of the present invention and the concomitant drug is not restricted, and the compound of the present invention and the concomitant drug may be administered to an administration subject simultaneously, or may be administered at different times. The dosage of the concomitant drug may be determined according to the dose clinically used, and may be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100 wt %, preferably about 0.1 to 50 wt %, further preferably about 0.5 to 20 wt %, of the whole preparation.

While the content of the additive such as a carrier in the combination agent of the present invention varies depending on the form of a preparation, it is generally about 1 to 99.99 wt %, preferably about 10 to 90 wt %, of the preparation.

When the compound of the present invention and the concomitant drug are separately prepared, the same content may be adopted.

While the dose varies depending on the kind of the compound of the present invention, administration route, symptom, age of patients and the like, for example, for an oral preparation to a patient (body weight about 60 kg) with chemotherapy-induced peripheral neuropathy (CIPN), chemotherapy-induced neuropathic pain (CINP), or liver failure and/or ischemia reperfusion injury (IRI), it is about 0.1 mg/kg body weight-about 30 mg/kg body weight, preferably about 1 mg/kg body weight-20 mg/kg body weight, as the compound of the present invention per one day, which is administered in one to several portions per day.

The dose of the medicament of the present invention as a sustained-release preparation varies depending on the kind and content of the compound of the present invention, dosage form, period of sustained drug release, subject animal of administration (e.g., mammals such as mouse, rat, hamster, guinea pig, rabbit, cat, dog, bovine, horse, swine, sheep, monkey and human), and administration object. For example, for application by parenteral administration, about 0.1 to about 100 mg of the compound of the present invention needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, dispensing of pharmaceuticals, kind of the pharmaceutical preparation, kind of active ingredient, and the like, and not particularly limited, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times divided in a day.

When the combination agent of the present invention is administered, the compound of the present invention and the concomitant drug can be administered simultaneously, or may be administered in a staggered manner. When administered in a staggered manner, an interval varies depending on the active ingredient, dosage form and administration method, and, for example, when the concomitant drug is administered first, a method in which the compound of the present invention is administered within time range of from for 1 minute to 3 days, preferably from for 10 minutes to 1 day, more preferably from for 15 minutes to 1 hour, after administration of the concomitant drug is included. When the compound of the present invention is administered first, a method in which the concomitant drug is administered within time range of from for 1 minute to 1 day, preferably from for 10 minutes to 6 hours, more preferably from for 15 minutes to 1 hour after administration of the compound of the present invention is included.

EXAMPLE

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In HPLC (high performance liquid chromatography), "C18" means use of octadecyl-bonded silica gel. The ratios of elution solvents are volume mixing ratios, unless otherwise specified.

In the Examples, the following abbreviations are used.
MS: mass spectrum
[M+H]$^+$, [M−H]$^-$: molecular ion peak
N: N
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: ElectroSpray Ionization
APCI: Atmospheric Pressure Chemical Ionization
THF: tetrahydrofuran
DMF: N,N-dimethylformamide
mCPBA: m-chloroperbenzoic acid
DBU: 1,8-diazabicyclo[5.4.0]-7-undecene
tert-BuOK: potassium tert-butoxide
DIEA: N-ethyl-N-(1-methylethyl)propan-2-amine $^1$H NMR was measured by Fourier-transform NMR. For the analysis, ACD/SpecManager (trade name) and the like were used. Very broad proton peaks of a hydroxy group, an amino group and the like are not described.

MS was measured by LC/MS. As an ionization method, ESI method or APCI method was used. The data indicates those found. Generally, a molecular ion peak is observed. However, when a compound has a tert-butoxycarbonyl group, a peak free of a tert-butoxycarbonyl group or tert-butyl group may be observed as a fragment ion. When a compound has a hydroxyl group, a peak free of H$_2$O may be observed as a fragment ion. In the case of a salt, a molecular ion peak or a fragment ion peak of a free form is generally observed.

The unit of sample concentration (c) in optical rotation ($[\alpha]_D$) is g/100 mL.

As the elemental analysis values (Anal.), calculated values (Calcd) and measured values (Found) are described.

Example 1

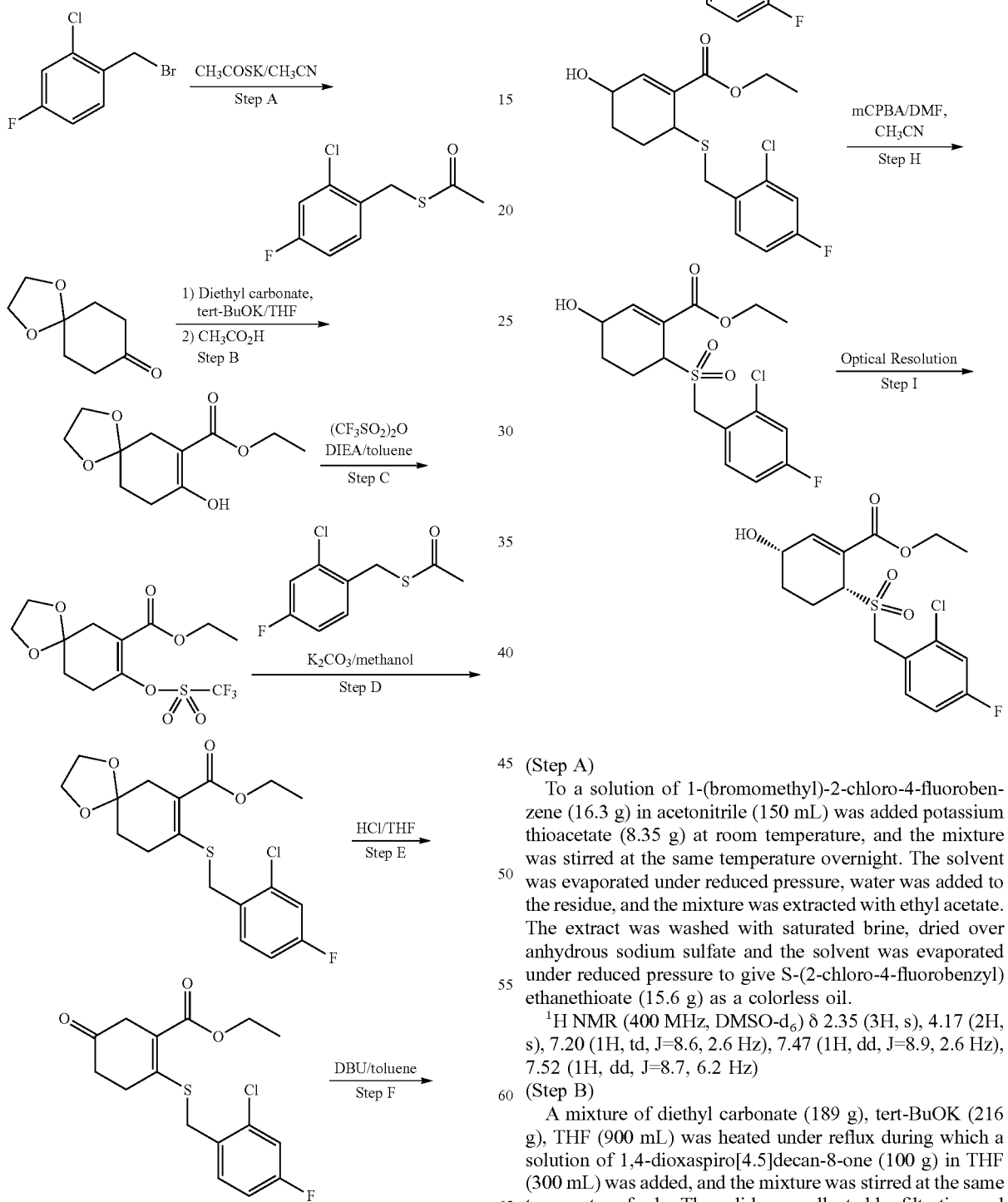

(Step A)

To a solution of 1-(bromomethyl)-2-chloro-4-fluorobenzene (16.3 g) in acetonitrile (150 mL) was added potassium thioacetate (8.35 g) at room temperature, and the mixture was stirred at the same temperature overnight. The solvent was evaporated under reduced pressure, water was added to the residue, and the mixture was extracted with ethyl acetate. The extract was washed with saturated brine, dried over anhydrous sodium sulfate and the solvent was evaporated under reduced pressure to give S-(2-chloro-4-fluorobenzyl) ethanethioate (15.6 g) as a colorless oil.

$^1$H NMR (400 MHz, DMSO-$d_6$) δ 2.35 (3H, s), 4.17 (2H, s), 7.20 (1H, td, J=8.6, 2.6 Hz), 7.47 (1H, dd, J=8.9, 2.6 Hz), 7.52 (1H, dd, J=8.7, 6.2 Hz)

(Step B)

A mixture of diethyl carbonate (189 g), tert-BuOK (216 g), THF (900 mL) was heated under reflux during which a solution of 1,4-dioxaspiro[4.5]decan-8-one (100 g) in THF (300 mL) was added, and the mixture was stirred at the same temperature for hr. The solid was collected by filtration and washed with ethyl acetate. The obtained solid was dissolved in water (100 mL), added under ice-cooling to a mixture of water (50 mL) and acetic acid (50 mL), and the mixture was extracted 3 times with ethyl acetate. The extract was washed with water (twice), aqueous saturated sodium hydrogen carbonate solution and saturated brine, dried over anhydrous magnesium sulfate and filtered through silica gel. The filtrate was concentrated under reduced pressure to give ethyl 8-hydroxy-1,4-dioxaspiro[4.5]dec-7-ene-7-carboxylate (101 g) as a pale-orange oil.

$^1$H NMR (300 MHz, DMSO-d$_6$) δ 1.13-1.21 (3H, m), 1.76 (2H, t, J=6.6 Hz), 2.33-2.42 (4H, m), 3.86-3.99 (6H, m), 12.14 (1H, s).

(Step C)

To a mixture of ethyl 8-hydroxy-1,4-dioxaspiro[4.5]dec-7-ene-7-carboxylate (115 g), DIEA (106 mL) and toluene (1008 mL) was added trifluoromethanesulfonic anhydride (124 mL) at −78° C., and the mixture was stirred at the same temperature for 1 hr. The reaction mixture was diluted with saturated aqueous saturated sodium hydrogen carbonate solution and stirred at room temperature for 30 min. After stirring, about a half amount of the organic solvent was evaporated under reduced pressure and the obtained mixture was extracted twice with ethyl acetate. The extract was washed with water and saturated brine, dried over anhydrous magnesium sulfate and the solvent was evaporated under reduced pressure to give ethyl 8-(((trifluoromethyl)sulfonyl) oxy)-1,4-dioxaspiro[4.5]dec-7-ene-7-carboxylate (181 g).

MS: [M+H]$^+$ 361.0.

(Step D)

To a mixture of ethyl 8-(((trifluoromethyl)sulfonyl)oxy)-1,4-dioxaspiro[4.5]dec-7-ene-7-carboxylate (10.0 g), S-(2-chloro-4-fluorobenzyl)ethanethioate (6.68 g) and methanol (100 mL) was added potassium carbonate (2.69 g) under a nitrogen atmosphere under ice-cooling, and the mixture was stirred at room temperature overnight. To the reaction mixture was added water (400 mL) and the resulting solid was collected by filtration. The obtained solid was washed with a mixture of ethyl acetate/hexane=1/4 to give ethyl 8-((2-chloro-4-fluorobenzyl)sulfanyl)-1,4-dioxaspiro[4.5]dec-7-ene-7-carboxylate (7.76 g) as a white solid.

$^1$H NMR (300 MHz, CDCl$_3$) δ 1.27 (3H, t, J=7.2 Hz), 1.83 (2H, t, J=6.6 Hz), 2.60 (2H, s), 2.67-2.83 (2H, m), 3.93-4.08 (4H, m), 4.12 (2H, s), 4.18 (2H, q, J=7.1 Hz), 6.95 (1H, td, J=8.1, 2.6 Hz), 7.11 (1H, dd, J=8.5, 2.5 Hz), 7.44 (1H, dd, J=8.7, 6.0 Hz).

(Step E)

To a solution of ethyl 8-((2-chloro-4-fluorobenzyl)sulfanyl)-1,4-dioxaspiro[4.5]dec-7-ene-7-carboxylate (7.76 g) in THF (80 mL) was added 6N hydrochloric acid (66.9 mL) under ice-cooling, and the mixture was stirred at room temperature overnight. To the reaction mixture was added water (300 mL), and the mixture was stirred at room temperature for 30 min. The resulting solid was collected by filtration, and washed with a mixture of ethyl acetate/hexane=1/4. The obtained solid was dissolved in acetonitrile and dried over anhydrous sodium sulfate. The solution was filtered and concentrated under reduced pressure to give ethyl 2-((2-chloro-4-fluorobenzyl)sulfanyl)-5-oxocyclohex-1-ene-1-carboxylate (6.38 g) as a white solid. MS: [M−H]$^-$ 340.9.

(Step F)

To a mixture of ethyl 2-((2-chloro-4-fluorobenzyl)sulfanyl)-5-oxocyclohex-1-ene-1-carboxylate (30.0 g) and toluene (300 mL) was added DBU (1.31 mL) under ice-cooling and the mixture was stirred at the same temperature for 1 hr. The reaction mixture was diluted with 0.1N hydrochloric acid and extracted with ethyl acetate. The extract was washed with saturated brine, dried over anhydrous sodium sulfate and the solvent was evaporated under reduced pressure. The residue was purified by silica gel column chromatography (ethyl acetate/hexane) to give ethyl 6-((2-chloro-4-fluorobenzyl)sulfanyl)-3-oxocyclohex-1-ene-1-carboxylate (25.9 g) as a yellow oil.

$^1$H NMR (300 MHz, CDCl$_3$) δ 1.31 (3H, t, J=7.2 Hz), 2.08-2.20 (1H, m), 2.23-2.37 (1H, m), 2.38-2.51 (1H, m), 2.91 (1H, ddd, J=17.4, 13.8, 5.1 Hz), 3.99 (2H, s), 4.03 (1H, t, J=3.2 Hz), 4.27 (2H, q, J=7.2 Hz), 6.60 (1H, s), 6.99 (1H, td, J=8.3, 2.6 Hz), 7.15 (1H, dd, J=8.7, 2.6 Hz), 7.43 (1H, dd, J=8.5, 5.9 Hz).

(Step G)

To a mixture of ethyl 6-((2-chloro-4-fluorobenzyl)sulfanyl)-3-oxocyclohex-1-ene-1-carboxylate (7.0 g), cerium (III) chloride (6.04 g) and ethanol (100 mL) was added under ice-cooling sodium borohydride (0.77 g), and the mixture was stirred at the same temperature for 1 hr. The reaction mixture was diluted with water at the same temperature and extracted three times with ethyl acetate. The extract was combined, washed with saturated brine, dried over anhydrous magnesium sulfate and the solvent was evaporated under reduced pressure. The residue was purified by silica gel column chromatography (ethyl acetate/hexane) to give cis-ethyl 6-((2-chloro-4-fluorobenzyl)sulfanyl)-3-hydroxycyclohex-1-ene-1-carboxylate (7.1 g) as a colorless oil. 1H NMR (300 MHz, CDCl$_3$) δ 1.27 (3H, t, J=7.2 Hz), 1.77-1.95 (3H, m), 1.98-2.07 (1H, m), 3.74 (1H, brs), 3.95 (2H, s), 4.20 (2H, q, J=7.2 Hz), 4.25-4.37 (1H, m), 6.79 (1H, brs), 6.92-7.01 (1H, m), 7.12 (1H, dd, J=8.7, 2.6 Hz), 7.43 (1H, dd, J=8.7, 6.0 Hz).

(Step H)

To a mixture of cis-ethyl 6-((2-chloro-4-fluorobenzyl) sulfanyl)-3-hydroxycyclohex-1-ene-1-carboxylate (3.03 g), acetonitrile (24 mL) and DMF (6 mL) was added mCPBA (4.84 g, 72%) under ice-cooling, and the mixture was stirred at the same temperature for 3 hr. The reaction mixture was diluted with saturated aqueous sodium thiosulfate solution and extracted with ethyl acetate. The extract was washed twice with saturated aqueous saturated sodium hydrogen carbonate solution and once with saturated brine, and dried over anhydrous sodium sulfate. The solvent was evaporated under reduced pressure. The residue was purified by silica gel column chromatography (ethyl acetate/hexane), and the obtained solid was washed with a mixture of hexane/ethyl acetate=1/1 to give cis-ethyl 6-((2-chloro-4-fluorobenzyl) sulfonyl)-3-hydroxycyclohex-1-ene-1-carboxylate (2.12 g) as a white solid.

$^1$H NMR (300 MHz, CDCl$_3$) δ 1.33 (3H, t, J=7.0 Hz), 1.74-2.05 (3H, m), 2.06-2.23 (1H, m), 2.41-2.56 (1H, m), 4.18-4.46 (4H, m), 4.61 (2H, s), 7.05 (1H, td, J=8.1, 2.6 Hz), 7.21 (1H, dd, J=8.7, 2.6 Hz), 7.25 (1H, s), 7.59 (1H, dd, J=8.5, 5.9 Hz).

(Step I)

cis-Ethyl 6-((2-chloro-4-fluorobenzyl)sulfonyl)-3-hydroxycyclohex-1-ene-1-carboxylate (2.14 g) was fractionated by HPLC (column: CHIRALPAK IC, 50 mmID×500 mmL, mobile phase: hexane/ethyl acetate=50/50, flow rate: 80 mL/min, column temperature: 30° C.). The first peak fraction was concentrated and recrystallized from ethyl acetate/hexane to give ethyl (3S,6R)-6-((2-chloro-4-fluorobenzyl)sulfonyl)-3-hydroxycyclohex-1-ene-1-carboxylate (0.73 g) as a white solid. Absolute steric configuration was determined by X-ray crystal structure analysis.

Optical purity>99.9% ee (analysis conditions column: CHIRALPAK IC, 4.6 mmID×250 mmL, mobile phase: hexane/ethyl acetate=30/70, flow rate: 1.0 mL/min, column temperature: 30° C.); $[\alpha]_D^{25}$+43.2 (c 0.312, $CH_3OH$);

mp 155-156° C.;

Anal. Calcd for $C_{16}H_{18}ClFO_5S$: C, 51.00; H, 4.81. Found: C, 50.95; H, 5.04.

Experimental Example 1 Suppressive Effect on NO Production

The suppressive activity on TLR4 was measured using mouse macrophage cell line RAW264.7 and by an inhibition ratio by the test compound (compound of Example 1) against NO produced by the addition of lipopolysaccharide (LPS). The cells were prepared at $2×10^6$ cells/ml in RPMI-1640 medium (phenol red free) supplemented with 10% inactivated fetal calf serum, and seeded in a 384-well plate at $6×10^4$ cells/30 µL per well. The cells were cultured overnight at 37° C. under 5% $CO_2$/95% air. The test compound dissolved in DMSO was diluted 200-fold with RPMI-1640 medium to a compound concentration of 500 nM. The prepared test compound (10 µL) was added to the cells (final concentration 10 nM), and LPS (Sigma Ltd.) and mouse interferon gamma (Wako Pure Chemical Industries, Ltd.) were respectively added by 10 µL to the final concentrations of 1.25 ng/ml and 0.2 ng/ml. After further culturing overnight, the concentration of nitrite ion (stable metabolite of NO) in the culture supernatant was measured and used as an index of NO production. The nitrite ion concentration was quantified by adding 10 µL of a solution of 20 µg/mL 2,3-diaminonaphthalene (DAN) in 0.2N HCl to the culture supernatant (20 µL), incubating the mixture at room temperature for 10 min, adding 0.5N NaOH (10 µL), and measuring 460 nm (excitation wavelength 355 nm) fluorescence value by a plate reader EnVision (PerkinElmer). The NO production inhibitory rate (%) was calculated using the value without addition of a stimulant as 100% inhibition control and the value without addition of the compound as 0% inhibition control. The results thereof are shown in Table 1.

TABLE 1

| compound | NO production suppression effect at 10 nM (% inhibition) |
|---|---|
| compound of Example 1 | 98 |

Experimental Example 2 Safety Test

The safety of the compound of the present invention can be confirmed, for example, by the following method. Three doses of the compound were intravenously administered singly to two male rats and two female rats of each group from the tail vein (administration rate: 1 mL/min), and life-or-death, general condition and body weight of the animals were examined. The observation period was one week after administration, and the medium was similarly administered to the control group.

Formulation Example 1 (Production of Capsule)

| 1) | Compound of Example 1: | 30 mg |
| 2) | Fine powder cellulose: | 10 mg |
| 3) | Lactose: | 19 mg |
| 4) | Magnesium stearate: | 1 mg |
| | Total | 60 mg |

1), 2), 3) and 4) are mixed and filled in a gelatin capsule.

Formulation Example 2 (Production of Tablet)

| 1) | Compound of Example 1: | 30 g |
| 2) | Lactose: | 50 g |
| 3) | Cornstarch: | 15 g |
| 4) | Carboxymethylcellulose calcium: | 44 g |
| 5) | Magnesium stearate: | 1 g |
| | 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has a Toll-like receptor 4 (TLR4) signaling inhibitory action, and may be useful as a prophylactic or therapeutic drug for diseases such as autoimmune diseases and/or inflammatory diseases, or chemotherapy-induced peripheral neuropathy (CIPN), chemotherapy-induced neuropathic pain (CINP), liver failure, and ischemia reperfusion injury (IRI).

This application is based on a patent application No. 2016-176545 filed in Japan (filing date: Sep. 9, 2016), the contents of which are incorporated in full herein.

The invention claimed is:

1. Ethyl 6-((2-chloro-4-fluorobenzyl)sulfonyl)-3-hydroxycyclohex-1-en-1-carboxylate or an optical isomer thereof.

2. Ethyl (3S,6R)-6-((2-chloro-4-fluorobenzyl)sulfonyl)-3-hydroxycyclohex-1-en- 1-carboxylate.

3. A medicament comprising the compound according to claim 1.

4. The medicament according to claim 3, which is a Toll-like receptor 4 inhibitor.

5. The medicament according to claim 3, which is a therapeutic agent for a disease related to the expression of Toll-like receptor 4, wherein the disease is an autoimmune disease and/or an inflammatory disease.

6. The medicament according to claim 3, which is a therapeutic agent for chemotherapy-induced peripheral neuropathy (CIPN), chemotherapy-induced neuropathic pain (CINP), liver failure and/or ischemia reperfusion injury (IRI).

7. The compound according to claim 1, which is used for treating a disease related to the expression of Toll-like receptor 4, wherein the disease is an autoimmune disease and/or an inflammatory disease.

8. The compound according to claim 1, which is used for treating chemotherapy-induced peripheral neuropathy (CIPN), chemotherapy-induced neuropathic pain (CINP), liver failure and/or ischemia reperfusion injury (IRI).

9. A method for inhibiting a Toll-like receptor 4 in a mammal, comprising administering an effective amount of the compound according to claim 1 to the mammal.

10. A method or treating a disease related to the expression of Toll-like receptor 4, wherein the disease is an autoimmune disease and/or an inflammatory disease in a mammal, comprising administering an effective amount of the compound according to claim 1 to the mammal.

11. A method for treating chemotherapy-induced peripheral neuropathy (CIPN), chemotherapy-induced neuropathic pain (CINP), liver failure and/or ischemia reperfusion injury (IRI) in a mammal, comprising administering an effective amount of the compound according to claim 1 to the mammal.

12. A medicament comprising the compound according to claim 2.

13. The medicament according to claim 12, which is a Toll-like receptor 4 inhibitor.

14. The medicament according to claim 12, which is a therapeutic agent for a disease related to the expression of Toll-like receptor 4, wherein the disease is an autoimmune disease and/or an inflammatory disease.

15. The medicament according to claim 14, which is a therapeutic agent for chemotherapy-induced peripheral neuropathy (CIPN), chemotherapy-induced neuropathic pain (CINP), liver failure and/or ischemia reperfusion injury (IRI).

16. The compound according to claim 2, which is used for treating a disease related to the expression of Toll-like receptor 4, wherein the disease is an autoimmune disease and/or an inflammatory disease.

17. The compound according to claim 2, which is used for treating chemotherapy-induced peripheral neuropathy (CIPN), chemotherapy-induced neuropathic pain (CINP), liver failure and/or ischemia reperfusion injury (IRI).

18. A method for inhibiting a Toll-like receptor 4 in a mammal, comprising administering an effective amount of the compound according to claim 2 to the mammal.

19. A method for treating a disease related to the expression of Toll-like receptor 4, wherein the disease is an autoimmune disease and/or an inflammatory disease in a mammal, comprising administering an effective amount of the compound according to claim 2 to the mammal.

20. A method for treating chemotherapy-induced peripheral neuropathy (CIPN), chemotherapy-induced neuropathic pain (CINP), liver failure and/or ischemia reperfusion injury (IRI) in a mammal, comprising administering an effective amount of the compound according to claim 2 to the mammal.

* * * * *